(12) United States Patent
Kim et al.

(10) Patent No.: US 10,822,472 B2
(45) Date of Patent: Nov. 3, 2020

(54) PLASTICIZER COMPOSITION AND RESIN COMPOSITION INCLUDING THE SAME

(71) Applicant: LG CHEM, LTD., Seoul (KR)

(72) Inventors: Hyun Kyu Kim, Daejeon (KR); Mi Yeon Lee, Daejeon (KR); Yun Ki Cho, Daejeon (KR); Jeong Ju Moon, Daejeon (KR); Joo Ho Kim, Daejeon (KR); Seok Ho Jeong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 23 days.

(21) Appl. No.: 16/076,638

(22) PCT Filed: Sep. 5, 2017

(86) PCT No.: PCT/KR2017/009680
§ 371 (c)(1),
(2) Date: Aug. 8, 2018

(87) PCT Pub. No.: WO2018/048169
PCT Pub. Date: Mar. 15, 2018

(65) Prior Publication Data
US 2019/0048167 A1 Feb. 14, 2019

(30) Foreign Application Priority Data
Sep. 7, 2016 (KR) .................. 10-2016-0115271

(51) Int. Cl.
| | | |
|---|---|---|
| *C08K 5/12* | (2006.01) | |
| *C07C 69/82* | (2006.01) | |
| *C08K 5/00* | (2006.01) | |
| *C08K 5/10* | (2006.01) | |
| *C08L 23/06* | (2006.01) | |
| *C08L 23/08* | (2006.01) | |
| *C08L 23/12* | (2006.01) | |
| *C08L 25/06* | (2006.01) | |
| *C08L 27/06* | (2006.01) | |
| *C08L 61/02* | (2006.01) | |
| *C08L 75/04* | (2006.01) | |
| *C07C 67/08* | (2006.01) | |
| *C07C 69/75* | (2006.01) | |

(52) U.S. Cl.
CPC .............. *C08K 5/12* (2013.01); *C07C 67/08* (2013.01); *C07C 69/75* (2013.01); *C07C 69/82* (2013.01); *C08K 5/00* (2013.01); *C08K 5/0016* (2013.01); *C08K 5/10* (2013.01); *C08L 23/06* (2013.01); *C08L 23/0853* (2013.01); *C08L 23/12* (2013.01); *C08L 25/06* (2013.01); *C08L 27/06* (2013.01); *C08L 61/02* (2013.01); *C08L 75/04* (2013.01)

(58) Field of Classification Search
None
See application file for complete search history.

(56) References Cited

U.S. PATENT DOCUMENTS

| | | | |
|---|---|---|---|
| 7,973,194 B1 | 7/2011 | Kinkade et al. | |
| 10,030,119 B2 | 7/2018 | Gourdin et al. | |
| 2005/0020718 A1* | 1/2005 | Gosse ..................... | C08K 5/12 523/105 |
| 2007/0179229 A1 | 8/2007 | Grass | |
| 2013/0303640 A1 | 11/2013 | Kim et al. | |
| 2013/0317152 A1 | 11/2013 | Becker et al. | |
| 2016/0237244 A1 | 8/2016 | Boeck et al. | |
| 2016/0326346 A1* | 11/2016 | Gourdin ................... | C08K 5/11 |

FOREIGN PATENT DOCUMENTS

| | | |
|---|---|---|
| EP | 1808457 B | 7/2008 |
| EP | 2810982 A1 | 12/2014 |
| JP | 2003-277561 A | 10/2003 |
| JP | 2015-217608 A | 12/2015 |
| JP | 2015-223700 A | 12/2015 |
| JP | 2016-74876 A | 5/2016 |
| KR | 1020120083560 A | 7/2012 |
| KR | 10-1264148 B1 | 5/2013 |
| KR | 1020140005908 A | 1/2014 |
| KR | 10-2016-0101880 A | 8/2016 |
| WO | 2011/115757 A1 | 9/2011 |
| WO | 2014195055 A1 | 12/2014 |
| WO | 2014195056 A | 12/2014 |
| WO | 2015/101569 A1 | 7/2015 |

OTHER PUBLICATIONS

Database WPI: "Industrial-material sheet made of soft polyvinylchloride resin for e.g. canvas comprises flexible laminated body by which soft-polyvinylchloride-resin layer is provided on surface by using fiber fabric as base material", XP002786238, Thomson Scientific, Dec. 14, 2015 (Corresponds to JP2015-223700A).
Database WPI: "Industrial sheet made of soft PVC resin for e.g. truck hood covers comprises flexible laminated body containing soft PVC resin layer provided on surface of fiber fabric as base material", XP002786239, Thomson Scientific, Dec. 7, 2015 (Corresponds to JP2015-217608A).

* cited by examiner

*Primary Examiner* — Robert T Butcher
(74) *Attorney, Agent, or Firm* — Dentons US LLP

(57) ABSTRACT

The present invention relates to a plasticizer composition and a resin composition including the same, and can provide a plasticizer composition in which a terephthalate-based material and a cyclohexane 1,4-diester-based material are mixed, and the sum of carbon atoms of alkyl groups bonded to the two materials is in the range of 34 to 40, and by which environmental friendliness can be secured, mechanical properties such as tensile strength and an elongation rate and physical properties such as migration properties and volatile loss can be improved to levels equal to or higher than those of existing products, and effects of improving processability and plasticizing efficiency can be expected, and a resin composition including the same.

8 Claims, No Drawings

PLASTICIZER COMPOSITION AND RESIN COMPOSITION INCLUDING THE SAME

CROSS-REFERENCE TO RELATED APPLICATION

This application is a National Stage Application of International Application No. PCT/KR2017/009680, filed Sep. 5, 2017, and claims the benefit of Korean Patent Application No. 10-2016-0115271, filed on Sep. 7, 2016, contents of which are incorporated herein by reference in their entirety for all purposes as if fully set forth below.

TECHNICAL FIELD

The present invention relates to a plasticizer composition including a terephthalate of which the number of carbon atoms is restricted and the hydrogenated material thereof, and a resin composition including the same.

BACKGROUND ART

In general, an alcohol reacts with a polycarboxylic acid such as phthalic acid and adipic acid to form the corresponding ester in a plasticizer. Further, studies on plasticizer compositions capable of replacing phthalate plasticizers such as terephthalate-based, adipate-based, and other high-molecular-weight plasticizers have been continued in consideration of domestic and foreign regulations of phthalate plasticizers harmful to humans.

Further, there is a growing demand for the eco-friendly products in a plastisol industry such as flooring, wallpaper, soft and hard sheets and the like, a calendaring industry, and extrusion/injection compound industries. In order to enhance quality characteristics, processability and productivity of the finished product, it is necessary to use a suitable plasticizer in consideration of discoloration, migration properties, mechanical properties, etc.

Various supplementary materials such as plasticizers, fillers, stabilizers, viscosity reducing agents, dispersants, antifoaming agents, foaming agents and the like are added depending on the characteristics required by industry in the various areas of use, such as tensile strength, an elongation rate, light resistance, migration properties, gelling properties, an absorption rate, etc.

For example, among the plasticizer compositions applicable to PVC, when di(2-ethylhexyl) terephthalate, which is most commonly used at relatively low cost, is applied, hardness or sol viscosity is high, the absorption rate of the plasticizer is relatively slow, and migration properties and stress migration properties are poor.

A hydrogenated material of di(2-ethylhexyl) terephthalate may be considered as a solution for this problem, but migration properties and thermal stability are poor while plasticizing efficiency is improved, and manufacturing costs are increased due to the hydrogenation reaction, so that it is difficult to achieve economic efficiency.

In order to address the above-described issues, there is a continuing need for the development of new composition products including a material superior in physical properties to di(2-ethylhexyl) 1,4-cyclohexanoate which is hydrogenated di(2-ethylhexyl) terephthalate, or a novel derivative thereof, and studies on the development of products and applications of a vinyl chloride resin as an environmentally friendly plasticizer have been continued.

DISCLOSURE

Technical Problem

The present invention is directed to providing a plasticizer composition capable of improving poor physical properties caused by structural limitations, that is, a plasticizer composition which is eco-friendly, and has mechanical properties such as tensile strength and an elongation rate, physical properties such as migration properties, stress migration properties and volatile loss improved to levels equal to or higher than those of conventional products, and has improved processability and plasticizing efficiency.

Technical Solution

In order to achieve the above-described objective, according to an aspect of the present invention, there is provided a plasticizer composition, including: a terephthalate-based material which is a compound represented by the following Formula 1; and a cyclohexane 1,4-diester-based material which is a compound represented by the following Formula 2; wherein a weight ratio of the terephthalate-based material to the cyclohexane 1,4-diester-based material is in a range of 99:1 to 1:99.

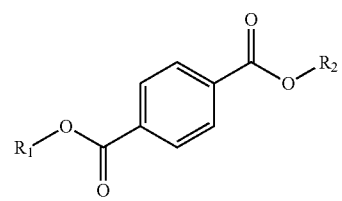

[Formula 1]

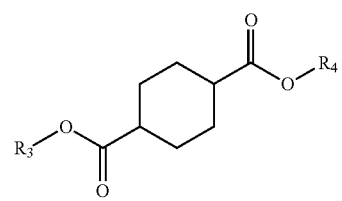

[Formula 2]

In Formulas 1 and 2, the $R_1$ to $R_4$ each independently represent an alkyl group having 8 to 10 carbon atoms, and a sum of carbon atoms of $R_1$ to $R_4$ is in a range of 34 to 40.

In order to achieve the above-described objective, according to another aspect of the present invention, there is provided a resin composition including a resin at 100 parts by weight; and the above-described plasticizer composition at 5 to 150 parts by weight.

The resin may be one or more selected from the group consisting of ethylene vinyl acetate, polyethylene, polypropylene, polyketone, polyvinyl chloride, polystyrene, polyurethane and a thermoplastic elastomer.

Advantageous Effects

When a plasticizer composition according to an embodiment of the present invention is used in a resin composition, environmental friendliness can be secured, mechanical properties such as tensile strength and an elongation rate and physical properties such as migration properties and volatile loss can be improved to levels equal to or higher than those of existing products, and effects of improving processability and plasticizing efficiency can be expected.

BEST MODE OF THE INVENTION

Hereinafter, the present invention will be described in detail in order to facilitate understanding of the present invention.

It should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation.

According to the present invention, a plasticizer composition includes a terephthalate-based material and a cyclohexane 1,4-diester-based material.

The terephthalate-based material may be a compound represented by the following Formula 1.

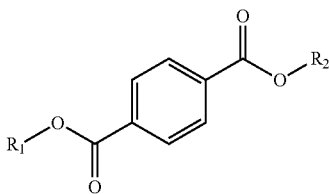

[Formula 1]

In Formula 1, $R_1$ and $R_2$ each independently represent an alkyl group having 8 to 10 carbon atoms.

Further, the cyclohexane 1,4-diester-based material may be a compound represented by the following Formula 2.

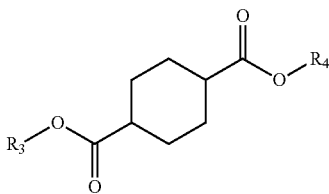

[Formula 2]

In Formula 2, $R_3$ and $R_4$ each independently represent an alkyl group having 8 to 10 carbon atoms.

Further, in Formulas 1 and 2, and a sum of carbon atoms of $R_1$ to $R_4$ is in the range of 34 to 40.

The substituent at the end of each of the terephthalate-based material and cyclohexane 1,4-diester-based material included in the plasticizer composition may be the same. That is, $R_1$ and $R_2$ may be the same, and $R_3$ and $R_4$ may be the same.

In the present specification, for example, when $R_3$ and $R_4$ are the same, the cyclohexane 1,4-diester-based material may refer to dialkyl cyclohexane-1,4-diester, and when $R_3$ and $R_4$ are different, the cyclohexane 1,4-diester-based material may refer to alkyl ($R_3$) alkyl ($R_4$) cyclohexane-1,4-diester.

In Formulas 1 and 2, $R_1$ to $R_4$ may each be independently the same or different, and may be an alkyl group having 8 to 10 carbon atoms, and preferably, may be branched. Specifically, $R_1$ to $R_4$ may each independently represent a 2-ethylhexyl group, an isononyl group, an isodecyl group or a 2-propylheptyl group.

Further, characteristically, the sum of the alkyl groups, that is, the sum of carbon atoms of $R_1$ to $R_4$, is required to be at least 34. Specifically, when $R_1$ and $R_2$ each represent an alkyl group having 8 carbon atoms, $R_3$ and $R_4$ each are required to be an alkyl group having at least 9 carbon atoms, and the sum of carbon atoms thereof may preferably be in the range of 34 to 40, and more preferably in the range of 36 to 40.

Further, when a terephthalate-based material and a cyclohexane 1,4-diester-based material which is a hydrogenated material of the terephthalate-based material are used together as in the plasticizer composition according to the present invention, there is a need to improve migration properties and thermal stability deteriorated due to hydrogenation, and it is required to maintain excellent properties such as tensile strength, an elongation rate, stress migration properties and volatile loss as well as improve migration properties and thermal stability by a terephthalate-based material mixed to reduce manufacturing costs increased due to hydrogenation.

However, di(2-ethylhexyl) cyclohexane-1,4-diester which is a hydrogenated material is mixed and used as a method of improving processability, plasticizing efficiency and mechanical properties of commonly used di(2-ethylhexyl) terephthalate to which an alkyl group having 8 carbon atoms is bonded, and in this case, although processability and plasticizing efficiency can be improved, excellent tensile strength, an elongation rate and low volatile loss characteristics at the excellent level of di (2-ethylhexyl) terephthalate are deteriorated, and thus it is difficult to say that the improvement is achieved in terms of overall plasticizer products.

In view of the problems as described above, in the present invention, the above-described physical properties can be improved by limiting the sum of carbon atoms of an alkyl group of the terephthalate-based material and cyclohexane 1,4-diester-based material to be in the range of 34 to 40.

Specifically, when the terephthalate-based material and the cyclohexane 1,4-diester-based material which is the hydrogenated material of the terephthalate-based material are mixed while the sum of carbon atoms of an alkyl group of each material is controlled to 34 or more, the tensile strength and elongation rate can be further improved, and the migration loss and volatile loss can be improved without a large loss in processability and plasticizing efficiency.

In the terephthalate-based material and cyclohexane 1,4-diester-based material, preferably, $R_1$ and $R_2$ are the same in Formula 1, and $R_3$ and $R_4$ are the same in Formula 2, and here, a substituent may preferably be a 2-ethylhexyl group, an isononyl group or a 2-propylheptyl group.

More preferably, the compound represented by Formula 1 may be a compound in which $R_1$ and $R_2$ are the same, and for example, may be a compound selected from the group consisting of di(2-ethylhexyl) terephthalate (DEHTP), diisononyl terephthalate (DINTP) and di(2-propylheptyl) terephthalate (DPHTP). When di(2-ethylhexyl) terephthalate is used as the terephthalate-based material, di(2-ethylhexyl) cyclohexane-1,4-diester may not be used as the cyclohexane 1,4-diester-based material.

Further, the compound represented by Formula 2 may be a compound in which $R_3$ and $R_4$ are the same, and for example, may be a compound selected from the group consisting of di(2-ethylhexyl) cyclohexane-1,4-diester (1,4-DEHCH), diisononyl cyclohexane-1,4-diester (1,4-DINCH) and di(2-propylheptyl) cyclohexane-1,4-diester(1,4-DPHCH). When di(2-ethylhexyl) cyclohexane-1,4-diester is used as the cyclohexane 1,4-diester-based material, di(2-ethylhexyl) terephthalate may not be used as the terephthalate-based material.

According to an embodiment of the present invention, the terephthalate-based material and cyclohexane 1,4-diester-based material may be included in a weight ratio of 99:1 to 1:99 in the plasticizer composition, and the upper limit of the ratio may be 99:1, and preferably 95:5, 90:10, 80:20 or 70:30, and the lower limit of the ratio may be 1:99, and preferably 30:70, or 40:60, and may be 50:50 or 60:40. Specifically, the weight ratio may be controlled from 99:1 to 1:99, 95:5 to 10:90, 90:10 to 10:90, 90:10 to 30:70 or 80:20 to 30:70.

When the terephthalate-based material and cyclohexane 1,4-diester-based material are characteristically mixed and used in the plasticizer composition as in the present invention, a plasticizer having excellent mechanical properties such as tensile strength and an elongation rate can be secured, thermal stability, stress migration properties, migration properties, volatility characteristics such as volatile loss and the like can be improved, and the effect of processability and plasticizing efficiency can be maximized when a cyclohexane 1,4-diester compound is used in combination.

Further, the plasticizer composition according to the present invention may not include a phthalate-based material. Generally, although the phthalate-based material has been used as a plasticizer that exhibits excellent physical properties, the phthalate-based material is classified as a substance that adversely affects the environment and the use thereof is limited. However, among the phthalate-based materials, while dioctyl phthalate (DOP) is registered as an environmentally regulated substance and the use thereof is extremely limited, diisononyl phthalate (DINP) or diisodecyl phthalate (DIDP) may be used in resin products which are not in contact with the human body depending on the use.

However, since the above-described phthalate-based material may not only cause environmental problems but also adversely affect the absorption rate of the plasticizer, and has a high possibility of adversely affecting migration properties, volatile loss and elongation rate characteristics, it is preferable that a phthalate-based material is not included in the plasticizer. Specifically, a phthalate-based material is generally not included in the plasticizer mainly used for eco-friendly products such as the above-described plasticizer composition.

According to an embodiment of the present invention, there is provided a method of preparing a plasticizer composition including: preparing a terephthalate-based material including a compound represented by the following Formula 1; preparing a cyclohexane 1,4-diester-based material including a compound represented by the following Formula 2 by performing a hydrogenation reaction of the terephthalate-based material in the presence of a metal catalyst; and blending the prepared terephthalate-based material with the hydrogenated cyclohexane 1,4-diester-based material.

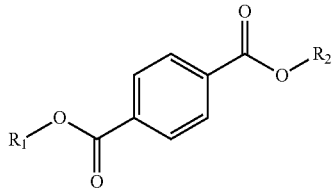

[Formula 1]

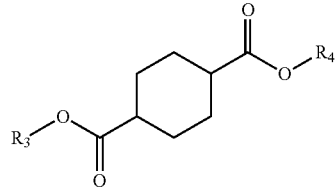

[Formula 2]

In Formulas 1 and 2, $R_1$ to $R_4$ each independently represent an alkyl group having 8 to 10 carbon atoms, and a sum of carbon atoms of $R_1$ to $R_4$ is in the range of 34 to 40.

The following preparation method is a method of preparing the above-described plasticizer composition, and has the same characteristics as that of the above-described plasticizer composition, unless specifically mentioned.

In the step of preparing the terephthalate-based material, the terephthalate-based material may be prepared by a direct esterification reaction, in which terephthalic acid reacts with an alcohol selected from the group consisting of a 2-ethylhexyl alcohol, an isononyl alcohol and a 2-propylheptyl alcohol.

The direct esterification reaction may be carried out by adding terephthalic acid to an alcohol and adding a catalyst thereto to perform a reaction under a nitrogen atmosphere; removing an unreacted alcohol and neutralizing an unreacted acid; and performing dehydration and filtration by vacuum distillation.

The alcohol may be used in an amount from 150 to 500 mol %, 200 to 400 mol %, 200 to 350 mol %, 250 to 400 mol % or 270 to 330 mol % based on 100 mol % of terephthalic acid.

Further, the catalyst, for example, may be selected one or more from acid catalysts such as sulfuric acid, hydrochloric acid, phosphoric acid, nitric acid, para-toluenesulfonic acid, methanesulfonic acid, ethanesulfonic acid, propanesulfonic acid, butanesulfonic acid and alkyl sulfuric acid, metal salts such as aluminum lactate, lithium fluoride, potassium chloride, cesium chloride, calcium chloride, iron chloride and aluminum phosphate, metal oxides such as heteropolyacids, natural/synthetic zeolites, cation and anion exchange resins, and organometallic compounds such as tetraalkyltitanate and polymers thereof. As a specific example, tetraalkyltitanate may be used as the catalyst.

The amount of catalyst used may vary depending on the type, and an amount of the used catalyst is for example, for a homogeneous catalyst, 0.01 to 5 wt %, 0.01 to 3 wt %, 1 to 5 wt % or 2 to 4 wt % based on 100 wt % of the total reactants, for a heterogeneous catalyst, 5 to 200 wt %, 5 to 100 wt %, 20 to 200 wt %, or 20 to 150 wt % based on 100 wt % of the total reactants.

The direct esterification reaction is performed at a temperature range of 80 to 270° C., preferably 150 to 250° C. for 10 minutes to 10 hours, preferably for 30 minutes to 8 hours, and more preferably for 1 to 6 hours. Within the above-described temperature and time ranges, a terephthalate-based material may be effectively obtained.

The hydrogenation reaction step may be a step of performing a hydrogenation reaction of the terephthalate-based material in the presence of a metal catalyst to partially convert the terephthalate-based material into a cyclohexane 1,4-diester-based material, thereby preparing the plasticizer composition in the form of a mixture.

As the terephthalate-based material used in the hydrogenation reaction, a material prepared in the step of preparing the terephthalate-based material may be used, or a commercially available terephthalate-based material may be purchased and used.

The reaction of the hydrogenation reaction step is a reaction for eliminating a double bond of a benzene ring of the terephthalate-based materials by adding hydrogen in the presence of a metal catalyst, and may be a kind of reduction reaction.

The hydrogenation reaction is for synthesizing the cyclohexane 1,4-diester-based material by carrying out a reaction of the terephthalate-based material with hydrogen in the presence of the metal catalyst, and the reaction conditions thereof may include all of the usual reaction conditions in which only the benzene ring can be hydrogenated without affecting a carbonyl group substituted in the benzene.

The hydrogenation reaction may be carried out by further including an organic solvent such as ethanol, but is not limited thereto. Examples of the metal catalyst include a Rh/C catalyst, a Pt catalyst, a Pd catalyst and the like which are generally used for hydrogenating the benzene ring, but are not limited thereto as long as the hydrogenation reaction as described above can be carried out.

Further, in the preparation of the cyclohexane 1,4-diester-based material, the cyclohexane 1,4-diester-based material may be prepared by a method of hydrogenating a terephthalate having an alkyl group with 9 or 10 carbon atoms as described above, but may also be prepared by a transesterification reaction in which dimethyl cyclohexane-1,4-diester prepared by hydrogenating dimethyl terephthalate reacts with an alcohol having an alkyl group with 9 or 10 carbon atoms, or a direct esterification reaction in which cyclohexane-1,4-dicarboxylic acid prepared by hydrogenating terephthalic acid reacts with an alcohol having an alkyl group with 9 or 10 carbon atoms.

In the present invention, a method of preparing a plasticizer composition in which a terephthalate-based material and the cyclohexane 1,4-diester-based material are mixed is not particularly limited.

According to another embodiment of the present invention, there is provided a resin composition including the above-described plasticizer composition and a resin.

The resin may include known resins in the related field. For example, a mixture of at least one selected from the group consisting of ethylene vinyl acetate, polyethylene, polypropylene, polyvinyl chloride, polystyrene, polyurethane, a thermoplastic elastomer and polylactic acid may be used, but the resin is not limited thereto.

The plasticizer composition may be included at 5 to 150 parts by weight, preferably 5 to 100 parts by weight, or 10 to 70 parts by weight based on 100 parts by weight of the resin.

Generally, a resin in which the plasticizer composition is used may be manufactured into a resin product through melt processing or plastisol processing, and the melt-processed resin and the plastisol-processed resin may be produced differently depending on each polymerization method.

For example, when polyvinyl chloride is used for melt processing, since a resin is prepared by suspension polymerization, solid resin particles having a large average particle size are used. When polyvinyl chloride is used for plastisol processing, since a resin is prepared by emulsion polymerization or the like, a resin in a sol state is used as fine resin particles, and materials which act as fillers are generally further included in the plastisol processing.

The plasticizer composition according to the present invention may be suitable for the melt-processed resin, and when used in plastisol processing, migration properties and gelling properties may be deteriorated, thereby reducing processability and/or productivity. Thus, the plasticizer composition is preferably mixed with a resin used for melt processing. For example, the melt processing may be a processing method such as extrusion molding, injection molding, calendaring molding.

The resin composition may further include a filler. The filler may be included at 0 to 300 parts by weight, preferably, 50 to 200 parts by weight, and more preferably, 100 to 200 parts by weight based on 100 parts by weight of the resin.

The filler may include known fillers in the related field, and is not limited thereto. For example, the filler may be a mixture of at least one selected from the group consisting of silica, magnesium carbonate, calcium carbonate, calcium carbonate, hard coal, talc, magnesium hydroxide, titanium dioxide, magnesium oxide, calcium hydroxide, aluminum hydroxide, aluminum silicate, magnesium silicate and barium sulfate.

Further, the resin composition may further include another additive such as a stabilizer as necessary. The other additive such as the stabilizer may be included by 0 to 20 parts by weight, and preferably 1 to 15 parts by weight based on 100 parts by weight of the resin.

For example, the stabilizer may include a calcium-zinc (Ca—Zn)-based stabilizer such as calcium-zinc complex stearate, but is not limited thereto.

MODES OF THE INVENTION

Examples

Hereinafter, exemplary embodiments of the present invention will be described. However, the embodiments of the present invention may be modified into a variety of different forms, and the scope of the present invention is not limited to the embodiments which will be described below. Further, the embodiments of the present invention are provided for the purpose of more fully describing the present invention to those skilled in the art.

Preparation Example 1: Preparation of di(2-ethylhexyl) terephthalate (DEHTP)

498.0 g of purified terephthalic acid (PTA), 1170 g of 2-ethylhexyl alcohol (2-EH) (molar ratio of PTA:2-EH=1.0:3.0) and 1.54 g of a titanium-based catalyst (TIPT, tetra isopropyl titanate)(0.31 parts by weight based on 100 parts by weight of PTA) as a catalyst were added to a 3 L four-neck reactor equipped with a cooler, a condenser, a decanter, a reflux pump, a temperature controller, a stirrer and the like, and a temperature was slowly raised to about 170° C. The generation of water was initiated at about 170° C., and an esterification reaction was conducted for about 4.5 hours while continuously introducing nitrogen gas at a reaction temperature of about 220° C. under atmospheric pressure. The reaction was terminated when an acid value reached 0.01.

After the completion of the reaction, distillation extraction was performed for 0.5 hours to 4 hours under reduced pressure in order to remove unreacted raw materials. Steam extraction was performed for 0.5 to 3 hours under reduced pressure using steam in order to remove the unreacted raw materials to below a predetermined content level. A temperature of a reaction solution was cooled to about 90° C. to perform a neutralization treatment using an alkaline solution. In addition, washing may be further performed and then water is removed by dehydrating the reaction solution.

Filter media were introduced into the dehydrated reaction solution and stirred for a predetermined time. Then, the solution was filtered to finally obtain 1326.7 g (yield: 99.0%) of DEHTP.

Preparation Example 2: Preparation of diisononyl terephthalate (DINTP)

1,243 g (yield: 99.0%) of DINTP was finally obtained in the same manner as in Preparation Example 1 except that isononyl alcohol instead of 2-ethylhexyl alcohol was added in the same molar ratio.

Preparation Example 3: Preparation of di(2-propylheptyl) terephthalate (DPHTP)

1,327 g (yield: 99.0%) of DPHTP was finally obtained in the same manner as in Preparation Example 1 except that 2-propylheptyl alcohol instead of 2-ethylhexyl alcohol was added in the same molar ratio.

Preparation Example 4: Preparation of di(2-ethylhexyl) cyclohexane-1,4-diester (1,4-DEHCH)

1000 g of di(2-ethylhexyl) terephthalate prepared in Preparation Example 1 and 20 g of a ruthenium catalyst (N.E CHEMCAT) were charged in a 1.5 L high-pressure reactor, hydrogen was added to a pressure of 8 MPa and a hydrogenation reaction was carried out at a temperature of 150° C. for 3 hours to complete the reaction. After completion of the reaction, the catalyst was filtered, and 1,4-DEHCH hydrogenated at a purity of 99.5% was prepared through a conventional purification process.

Preparation Example 5: Preparation of diisononyl cyclohexane-1,4-diester (1,4-DINCH)

Hydrogenated 1,4-DEHCH was obtained by performing a hydrogenation reaction in the same manner as in Preparation Example 4 except that the terephthalate prepared in Preparation Example 2 was used.

Preparation Example 6: Preparation of di(2-propylheptyl) cyclohexane-1,4-diester (1,4-DPHCH)

Hydrogenated 1,4-DEHCH was obtained by performing a hydrogenation reaction in the same manner as in Preparation Example 4 except that the terephthalate prepared in Preparation Example 3 was used.

Examples 1 to 7, Reference Example 1 and Comparative Examples 1 to 6: Mixed Plasticizer Composition Examples 1 to 7 and Comparative Examples 1 to 6 were composed by using mixtures prepared by the method of sequentially applying the materials of Preparation Examples 1 to 4 and each of the preparation methods as shown in the following Table 1.

In the following table, in addition to the materials prepared in Preparation Examples 1 to 6, dibutyl terephthalate, dibutyl cyclohexane-1,4-diester and di-dodecyl terephthalate manufactured by LG Chemical Co., Ltd. were used.

TABLE 1

|  | TP | Hydrogenated TP | Mixing ratio |
|---|---|---|---|
| Example 1 | DEHTP | DINCH | 6:4 |
| Example 2 | DINTP | DEHCH | 7:3 |
| Example 3 | DINTP | DINCH | 7:3 |
| Example 4 | DINTP | DINCH | 5:5 |
| Example 5 | DPHTP | DPHCH | 6:4 |
| Example 6 | DPHTP | DPHCH | 4:6 |
| Example 7 | DINTP | DPHCH | 3:7 |
| Reference Example 1 | DEHTP | — | — |
| Comparative Example 1 | DINTP | — | — |
| Comparative Example 2 | DPHTP |  | — |
| Comparative Example 3 | DEHTP | DEHCH | 5:5 |
| Comparative Example 4 | DBTP | DEHCH | 5:5 |
| Comparative Example 5 | DEHTP | DBCH | 5:5 |
| Comparative Example 6 | DUDTP | DEHCH | 7:3 |

Experimental Example 1: Evaluation of Physical Properties

Experimental specimens were prepared using the plasticizer compositions of the examples, reference examples and comparative examples listed in Table 1 above.

In the preparation of the experimental specimens, 40 parts by weight of plasticizer compositions of Examples 1 to 7, Reference Example 1 and Comparative Examples 1 to 6, and 3 parts by weight of a stabilizer (BZ-153T) were mixed at 98° C. and 700 rpm in 100 parts by weight of PVC (LS100S) using a 3 L super mixer based on ASTM D638. A 5 mm sheet was prepared by processing using a roll mill at 160° C. for 4 minutes. After pressing processes at 180° C. for 2.5 minutes at a low pressure and for 2 minutes at a high pressure, 1 T and 3 T sheets were prepared as specimens. The physical properties of each specimen were evaluated according to the following test items, and the results are summarized in the following Table 2.

<Test Items>

Hardness

Shore hardness (Shore "A" and Shore "D") 3 T 10 s was measured at 25° C. in accordance with ASTM D2240.

Tensile Strength

A breaking point of a specimen was measured after pulling the specimen at a cross-head speed of 200 mm/min (1 T) using a test instrument, U.T.M (model no; 4466, manufactured by Instron Corporation) according to the method of ASTM D638. The tensile strength was calculated as follows.

Tensile strength (kgf/mm$^2$)=Load value (kgf)/Thickness (mm)×width (mm)

Elongation Rate Measurement

A breaking point of a specimen was measured after pulling the specimen at a cross-head speed of 200 mm/min (1 T) using the U.T.M according to the method of ASTM D638, and the elongation rate was calculated as follows.

Elongation rate (%)=Length after elongation/Initial length×100

Migration Loss Measurement

A specimen having a thickness of 2 mm or more was obtained in accordance with KSM-3156. Glass plates were attached to both sides of the specimen, and a load of 1 kgf/cm² was then applied thereto. The specimen was left standing for 72 hours in a hot air circulating oven (80° C.), and cooled at room temperature for 4 hours. Thereafter, the glass plates attached to the both sides of the specimen were removed. Then, weights of the glass plates and specimen plate before and after being left standing in the oven were measured, and the migration loss was calculated by the following equation.

Migration loss (%)={(Initial weight of a specimen at room temperature−Weight of the specimen after being left standing in an oven)/Initial weight of the specimen at room temperature}×100

Volatile Loss Measurement

The specimen thus prepared was processed at 80° C. for 72 hours, and the weight of the specimen was measured.

Volatile loss (wt %)=Initial weight of a specimen−(Weight of the specimen after processing at 80° C. for 72 hours)/Initial weight of the specimen× 100

Absorption Rate Measurement

A resin and a plasticizer were mixed by using a planetary mixer (Brabender, P600) under mixing conditions of 77° C. and 60 rpm. The time period from mixing the resin and the plasticizer to obtaining a stabilized state of the torque of the mixer was measured and evaluated.

that an absorption rate of about 4 minutes to 7 minutes and 30 seconds is excellent. Considering the application of the plasticizer composition, preferably, it may be evaluated that an absorption rate of about 5 minutes to 7 minutes is excellent.

Referring to Table 2, it can be confirmed that the physical properties of Examples 1 to 7 were all improved to the same or higher level based on the level of physical properties of Reference Example 1. The hardness is measured to be equal to or less than that of Reference Example 1, so that the plasticizing efficiency can be evaluated to be improved to some extent, and as the absorption rate is also similar, it can be confirmed that there is no problem in processability. However, it was confirmed that the tensile strength and elongation rate were greatly increased as compared with Reference Example 1, and thereby it was confirmed that the plasticizer with improved performance can be provided by improving the mechanical properties while maintaining processability and plasticizing efficiency at the same level or more.

Further, it can be seen that, in the case of the terephthalate-alone plasticizer compositions of Comparative Examples 1 and 2, although volatile loss was lower than those of the examples, plasticizing efficiency was somewhat poor due to the relatively high hardness, and the loss of

TABLE 2

|  | Hardness (Shore A) | Hardness (Shore D) | Tensile strength (kg/cm³) | Elongation rate (%) | Migration loss (%) | Volatile loss (%) | Absorption rate (m:s) |
| --- | --- | --- | --- | --- | --- | --- | --- |
| Example 1 | 86.8 | 47.2 | 243.5 | 312.3 | 2.30 | 2.02 | 5:30 |
| Example 2 | 89.3 | 47.8 | 238.9 | 316.0 | 1.98 | 1.68 | 6:20 |
| Example 3 | 90.8 | 49.6 | 244.6 | 315.8 | 2.57 | 1.29 | 6:34 |
| Example 4 | 89.2 | 48.5 | 245.8 | 308.0 | 2.60 | 1.42 | 6:05 |
| Example 5 | 91.5 | 51.2 | 257.2 | 325.7 | 3.02 | 1.10 | 7:25 |
| Example 6 | 91.4 | 51.4 | 248.4 | 320.1 | 3.58 | 1.32 | 7:00 |
| Example 7 | 90.5 | 49.9 | 249.6 | 310.0 | 3.20 | 1.30 | 6:45 |
| Reference Example 1 | 90.7 | 50.2 | 227.9 | 279.6 | 2.57 | 2.64 | 6:15 |
| Comparative Example 1 | 92.9 | 52.8 | 240.0 | 283.7 | 4.21 | 0.98 | 7:45 |
| Comparative Example 2 | 95.4 | 55.7 | 241.5 | 287.5 | 4.58 | 0.96 | 13:20 |
| Comparative Example 3 | 87.0 | 47.5 | 215.7 | 265.0 | 3.56 | 5.64 | 5:30 |
| Comparative Example 4 | 82.3 | 42.5 | 187.6 | 235.4 | 8.58 | 17.85 | 3:27 |
| Comparative Example 5 | 84.4 | 43.6 | 209.8 | 238.0 | 6.80 | 12.56 | 4:15 |
| Comparative Example 6 | 98.8 | 57.7 | 250.4 | 220.4 | 4.87 | 0.67 | 17:40 |

Reference Example 1 is a representative commercial product which is a commercially available general plasticizer replacing the phthalate plasticizer, but does not satisfy both the plasticizing efficiency and processability, and is a typical example of a product requiring improvement in mechanical properties.

Further, for reference, the absorption rate represents the rate at which the plasticizer is absorbed into the resin, which is an indicator for confirming processability. For example, when the plasticizer is absorbed too quickly, it may adversely affect a process of processing the resin due to an increase in viscosity and resin composition aggregation, and when the plasticizer is absorbed too slowly, since the processing time may be delayed, not only the productivity of the whole process may be reduced, but also processability may be reduced because the temperature is required to increase during mixing. In the present invention, it may be evaluated mechanical properties was inevitable due to the low elongation rate, and the absorption rate exceeds 7 minutes and 30 seconds, which may cause problems in processability. Particularly, in the case of Comparative Example 2, it can be seen that the plasticizer clearly has deteriorated processability since the time taken for the plasticizer to be absorbed is very long. That is, it can be seen that the loss of other physical properties is considerable when the plasticizer compositions of Comparative Examples 1 and 2 are used considering the superiority of volatile loss even after accepting the loss.

For reference, the absorption rate represents the rate at which the plasticizer is absorbed into the resin, which is an indicator for confirming processability. For example, when the plasticizer is absorbed too quickly, it may adversely affect a process of processing the resin due to insufficient time for gelling, and when the plasticizer is absorbed too slowly, since the processing time may be delayed, not only the productivity of the whole process may be reduced but also processability may be reduced because the temperature is required to increase during mixing. In the present invention, it may be evaluated that an absorption rate of about 5 minutes to 7 minutes 30 seconds is excellent.

Further, in the case of Comparative Example 3 where the sum of carbon atoms of the alkyl groups of materials included in the plasticizer composition is less than 34, there is a considerable loss in the tensile strength and elongation rate, and volatile loss is considerably inferior, that is, higher than those of other examples, as compared with Examples 1 and 2 where the number of carbon atoms of the alkyl groups is 34. Accordingly, it can be confirmed that, when the terephthalate and the hydrogenation material thereof are mixed, the number of carbon atoms of the alkyl groups bonded to the two materials needs to exceed 34.

Further, in the case of Comparative Examples 4 and 5, the sum of carbon atoms of the alkyl groups is less than 34 in the plasticizer compositions as in the case of Comparative Example 3, and it can be confirmed that volatile loss is extremely inferior, that is, higher by 10 times or more as compared with the examples to an extent to offset excellent plasticizing efficiency. Moreover, the tensile strength and elongation rate are also very low, and the migration loss is also excessive, and thus all of the properties other than the plasticizing efficiency are found to be poor. Accordingly, it can be reaffirmed that the sum of carbon atoms of the alkyl groups of the two materials needs to be 34 or more.

In addition, since it can be confirmed that, in Comparative Example 6, the sum of carbon atoms of the alkyl groups of the two materials was more than 40, the plasticizing efficiency and processability were extremely poor, and the elongation rate was also significantly low, the sum of carbon atoms of the alkyl groups needs to be controlled to 34 to 40.

While the present invention has been described in connection with exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A plasticizer composition, comprising:
a terephthalate-based material which is a compound represented by the following Formula 1; and
a cyclohexane 1,4-diester-based material which is a compound represented by the following Formula 2,
wherein a weight ratio of the terephthalate-based material to the cyclohexane 1,4-diester-based material is in a range of 7:3 to 3:7:

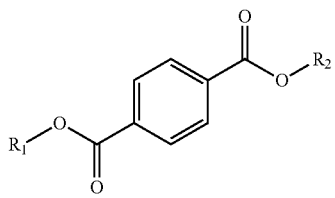

[Formula 1]

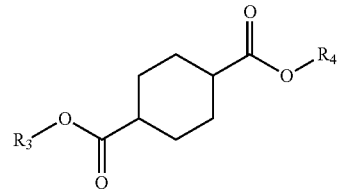

[Formula 2]

wherein in Formulas 1 and 2, $R_1$ to $R_4$ each independently represent an alkyl group having 8 to 10 carbon atoms, and a sum of carbon atoms of $R_1$ to $R_4$ is in a range of 34 to 40.

2. The plasticizer composition according to claim 1, wherein the plasticizer composition does not include a phthalate-based material.

3. The plasticizer composition according to claim 1, wherein, in Formulas 1 and 2, $R_1$ to $R_4$ each are independently selected from the group consisting of a 2-ethylhexyl group, an isononyl group, a 2-propylheptyl group and an isodecyl group.

4. The plasticizer composition according to claim 1, wherein the terephthalate-based material is one selected from the group consisting of di(2-ethylhexyl) terephthalate, diisononyl terephthalate (DEHTP), diisononyl terephthalate (DINTP) and di(2-propylheptyl) terephthalate (DPHTP), and when the terephthalate-based material is di(2-ethylhexyl) terephthalate, the cyclohexane 1,4-diester-based material is not di(2-ethylhexyl) cyclohexane 1,4-dicarboxylate (1,4-DEHCH).

5. The plasticizer composition according to claim 1, wherein the cyclohexane 1,4-diester-based material is one selected from the group consisting of di(2-ethylhexyl) cyclohexane 1,4-dicarboxylate (1,4-DEHCH), diisononyl cyclohexane 1,4-dicarboxylate (1,4-DINCH) and di(2-propylheptyl) cyclohexane-1,4-diester (1,4-DPHCH), and when the cyclohexane 1,4-diester-based material is di(2-ethylhexyl) cyclohexane 1,4-dicarboxylate (1,4-DEHCH), the terephthalate-based material is not di(2-ethylhexyl) terephthalate.

6. A resin composition, comprising a resin at 100 parts by weight; and the plasticizer composition according to claim 1 at 5 to 150 parts by weight.

7. The resin composition according to claim 6, wherein the resin is one or more selected from the group consisting of ethylene vinyl acetate, polyethylene, polypropylene, polyketone, polyvinyl chloride, polystyrene, polyurethane and a thermoplastic elastomer.

8. The plasticizer composition according to claim 1, wherein, in Formulas 1 and 2, a sum of carbon atoms of $R_1$ to $R_4$ is in a range of 36 to 40.

* * * * *